United States Patent
Zipplies et al.

(10) Patent No.: US 10,358,402 B2
(45) Date of Patent: Jul. 23, 2019

(54) PROCESS AND APPARATUS FOR PRODUCING FLUORINATED ALKENES

(71) Applicant: 3M INNOVATIVE PROPERTIES COMPANY, St. Paul, MN (US)

(72) Inventors: Tilman C. Zipplies, Burghausen (DE); Klaus Hintzer, Kastl (DE); Monika A. Willert-Porada, Bayreuth (DE); Thorsten Gerdes, Eckersdorf (DE); Jens Herdegen, Bayreuth (DE); Achim Schmidt-Rodenkirchen, Bayreuth (DE); Stephan Aschauer, Bayreuth (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 15/516,124

(22) PCT Filed: Sep. 30, 2015

(86) PCT No.: PCT/US2015/053281
§ 371 (c)(1),
(2) Date: Mar. 31, 2017

(87) PCT Pub. No.: WO2016/054246
PCT Pub. Date: Apr. 7, 2016

(65) Prior Publication Data
US 2017/0305820 A1   Oct. 26, 2017

(30) Foreign Application Priority Data
Oct. 1, 2014 (EP) .................................... 14187332

(51) Int. Cl.
C07C 17/361    (2006.01)
C07C 17/23    (2006.01)
(Continued)

(52) U.S. Cl.
CPC ........... C07C 17/361 (2013.01); B01J 19/088 (2013.01); B01J 19/126 (2013.01); C07C 17/23 (2013.01);
(Continued)

(58) Field of Classification Search
CPC ..... C07C 17/367; C07C 21/18; C07C 21/185; D06M 14/18; D06M 10/025
See application file for complete search history.

(56) References Cited

U.S. PATENT DOCUMENTS

| 2,709,182 A | 5/1955 | Farlow |
| 2,709,192 A | 5/1955 | Farlow |

(Continued)

FOREIGN PATENT DOCUMENTS

| WO | WO 1999-59385 | 11/1999 |
| WO | WO 2010-039820 | 4/2010 |

OTHER PUBLICATIONS

Hrycak, "Tuning Characteristics of Coaxial Microwave Plasma Source Operated With Argon, Nitrogen and Methane At Atmospheric Pressure", 2012, pp. 310-312.

(Continued)

*Primary Examiner* — Jafar F Parsa
(74) *Attorney, Agent, or Firm* — Thomas M. Spielbauer

(57) ABSTRACT

Provided is a process for producing fluorinated alkenes by providing a microwave plasma in a reactor chamber, introducing a protective gas feed into the reactor chamber, and contacting a conversion feed comprising at least one fluorinated linear or branched alkane with the plasma. Also provided are an apparatus and the use of the process and the apparatus.

13 Claims, 3 Drawing Sheets

(51) Int. Cl.
  *B01J 19/12* (2006.01)
  *B01J 19/08* (2006.01)
  *C07C 21/185* (2006.01)

(52) U.S. Cl.
  CPC ............... *B01J 2219/0875* (2013.01); *B01J 2219/0896* (2013.01); *B01J 2219/1206* (2013.01); *B01J 2219/1293* (2013.01)

(56) References Cited

U.S. PATENT DOCUMENTS

| | | |
|---|---|---|
| 2,902,521 A | 9/1959 | Cleaver |
| 3,009,966 A | 11/1961 | Hauptschein |
| 3,081,245 A | 3/1963 | Farlow |
| 3,133,871 A | 5/1964 | Tress |
| 3,471,546 A | 10/1969 | Bjornson |
| 3,904,501 A | 9/1975 | Lagow |
| 4,849,554 A | 7/1989 | Cresswell |
| 4,898,645 A | 2/1990 | Voigt |
| 4,973,773 A | 11/1990 | Malone |
| 5,611,896 A | 3/1997 | Swanepoel |
| 6,624,337 B1 | 9/2003 | Manzer |
| 6,919,015 B2 | 7/2005 | Bauer |
| 7,622,693 B2 | 11/2009 | Foret |
| 2011/0184214 A1* | 7/2011 | Hintzer ............... C07C 17/367 570/136 |

OTHER PUBLICATIONS

International Search Report for PCT International Application No. PCT/US2015/053281, dated Dec. 9, 2015, 4 pages.
India Examination Report for application No. 201747011972, dated Jan. 29, 2019, 6 pages.
Hempel, Maximilian, "Abschlussbericht Prozessund Reaktorentwicklung fur die plasmaunterstOtzte chlorfreie TFE Synthese, Aktenzeichen 28227-31, Projekttrager Deutsche Bundesstiftung Umwelt", XP055173051, Nov. 29, 2012, pp. 1-6 and 54-69.

\* cited by examiner

PROCESS AND APPARATUS FOR PRODUCING FLUORINATED ALKENES

CROSS REFERENCE TO RELATED APPLICATIONS

This application is a national stage filing under 35 U.S.C. 371 of PCT/US2015/053281, filed Sep. 30, 2015, which claims the benefit of European Application No. 14187332.3, filed Oct. 1, 2014, the disclosure of which is incorporated by reference in their entirety herein.

TECHNICAL FIELD

The present application relates to a process for producing fluorinated alkenes by means of a microwave plasma, an apparatus for producing fluorinated alkenes as well as the use of the process and the apparatus.

BACKGROUND ART

Olefinic hydrocarbon monomers for the synthesis of conventional mass polymers such as polyethylene and polypropylene are typically obtained by a steam cracking process.

In contrast, fluorinated olefin monomers such as tetrafluoroethylene (TFE) and hexafluoropropylene (HFP) as well as vinylidene fluoride or vinyl fluoride, which are required for the production of partially and fully fluorinated (perfluorinated) polymers (fluoropolymers) are currently only accessible via an intricate multi-stage process on industrial scale. Said process involves chlorine chemistry, and it requires rather high amounts of energy which is a drawback with regard to environmental as well as economical aspects. Further, numerous chlorinated intermediates and side-products are generated, and an expensive disposal of large quantities of aqueous hydrochloric acid waste contaminated with hydrofluoric acid is required. Additionally, in many countries around the world, regulatory bodies do not allow TFE to be transported due to its tendency to explode spontaneously, which requires a direct further processing at the production site.

Due to their exceptional properties, fluoropolymers cannot be substituted in high-tech applications such as in the semiconductor sector, in electrical/electronic systems, as seals and corrosion-resistant material in the field of environmental protection, and in technologies of energy conversion, e.g., fuel cells. Fluoropolymers allow continuous operating temperatures of above 280° C., are typically non-flammable, exhibit a high dielectric strength and low dielectric loss, good mechanical and sliding properties, inert behavior, and biocompatibility.

The state of the art process for producing TFE and HFP uses chlorodifluoromethane (R-22) as an intermediate and is based on chlorine, methane, and hydrofluoric acid. In a first step, trichloromethane as well as numerous undesired side-products are obtained by partial chlorination of methane, the trichloromethane then being further processed with hydrofluoric acid in the presence of an antimony chloride catalyst to yield chlorodifluoromethane. The latter compound is pyrolyzed in a third step at 800° C. to 900° C., and difluorocarbene obtained via elimination as an intermediate leads through subsequent dimerization to TFE. The process yields hydrochloric acid, different chloromethanes, antimony fluorides, and fluoromethanes. The R-22 pyrolysis is primarily carried out in tubular reactors only in the gas phase. Due to the endothermic reaction of about 64 KJ/mol, a temperature gradient occurs within the used tubular reactors, which results in a decrease of conversion and selectivity. Therefore, the yields in the reactors are only 30-40%, which, however, is intended, since at low conversions the selectivity to TFE is very high, and the formation of side-products can be reduced. However, the TFE synthesis through the R-22 route yields a large number of waste materials, which have to be processed, separated, and typically thermally recycled.

Therefore, new processes and reactors are needed which enable the production of the desired monomers, such as TFE and HFP, based on less reactive, chlorine-free starting materials, in particular from at least partially fluorinated or even perfluorinated paraffins, which, in turn, can be obtained on an industrial scale by electrochemical fluorination. The development of such new processes is required since the resulting fluoropolymers are of high importance for the production of special plastics as key components in the chemical technology, biotechnology, automotive and electronics industry. Further, the large amounts of aqueous hydrochloric acid waste being contaminated with hydrofluoric acid should be reduced or avoided.

As an alternative TFE synthesis based on the decomposition of fluorinated materials processes with high energy impact such as plasma or arc have been reported for example in U.S. Pat. Nos. 2,902,521, 2,709,182, 3,133,871, 2,709,192, 3,133,871, 3,009,966, 3,471,546, 3,904,501, 4,849,554, 4,898,645, 4,973,773, 5,611,896, WO 99/59385, U.S. Pat. Nos. 6,624,337, 7,622,693 and 6,919,015.

The fluorinated compounds to be decomposed to create fluoroalkenes can be obtained, for example, by electrochemical fluorination, starting from hydrofluoric acid and short-chain aliphatic compounds as known in the art. The processes for a chlorine-free TFE synthesis described above, however, have so far been of limited economical interest. Another route has been described in WO2010/039820 where fluorinated material is subjected to microwave irradiation in a fluidized bed reactor. However, there remains the need for a further process for producing fluorinated alkenes and an apparatus for such a process allows a synthesis with satisfying conversions and yields as a replacing for the R-22 route.

SUMMARY

In one aspect there is provided a process for producing fluorinated alkenes, the process comprising:
  a) providing a microwave plasma (0), forming a reaction zone (0'), in a reactor (1') comprising a reactor chamber (1) at least partially confined by a reactor wall (2) wherein the reactor chamber (1) has a substantially circular cross-section (4) with a diameter (5), and a length (6) being perpendicular to the cross-section (4) and being equal or greater than the diameter (5), and wherein the reactor chamber (1) has in its interior part (7) a longitudinal axis (8) running parallel to the length (6);
  b) providing a protective gas feed (9) in the reactor chamber (1), and
  c) contacting a conversion feed (10) comprising at least one fluorinated linear or branched alkane having from 1 to 10 carbon atoms with the plasma to produce a product stream (14) containing a fluorinated alkene;
    wherein the protective gas feed (9) in the reactor chamber (1) flows such that it creates or supports to create a reaction zone (0') that extends in its axial direction (12) along the longitudinal axis (8) of the reactor chamber (1) and is confined in its radial direction (11), which is perpendicular to its axial direction (12), to the central part of the reactor chamber (1) such that is does not contact the reactor wall (2).

In another aspect there is provided a reactor in a production line for producing a product stream (14) comprising fluorinated alkenes according to any one of the preceding claims, the reactor comprising a reactor chamber (1) confined by a reactor wall (2) wherein the reactor chamber (1) has a substantially circular cross-section (4) with a diameter (5) and a length (6) being perpendicular to the cross-section (4) and equal or greater than the diameter (5), and wherein the reactor chamber (1) has in its interior part (7) a longitudinal axis (8) running parallel to the length (6); the reactor further having at least one inlet (9a) for a protective gas feed (9) configured such that the protective gas feed (9) is introduced into the reactor chamber (1) at an angle with the longitudinal axis (8) of 45° to 110°, more preferably 75° to 90°; an inlet (10a) for a conversion feed (10) configured such that the conversion feed (10) is directed into along the longitudinal axis (8); at least one outlet (14a) directing the product stream (14) or of the reactor chamber (1).

DETAILED DESCRIPTION

It has been found that the present invention allows access to fluorinated alkenes such as TFE and HFP directly from linear or branched fluorinated alkanes. Thus, the intricate multi-step R-22 route can be avoided, which, in turn, leads also to the avoidance of the large quantities of undesired waste products connected with said process. In particular, as the present invention does not require any chlorine-containing compounds, the formation of side products such as hydrochloric acid or chlorofluorocarbons is substantially avoided and thus such side products do not need to be disposed of.

Figure 1B:
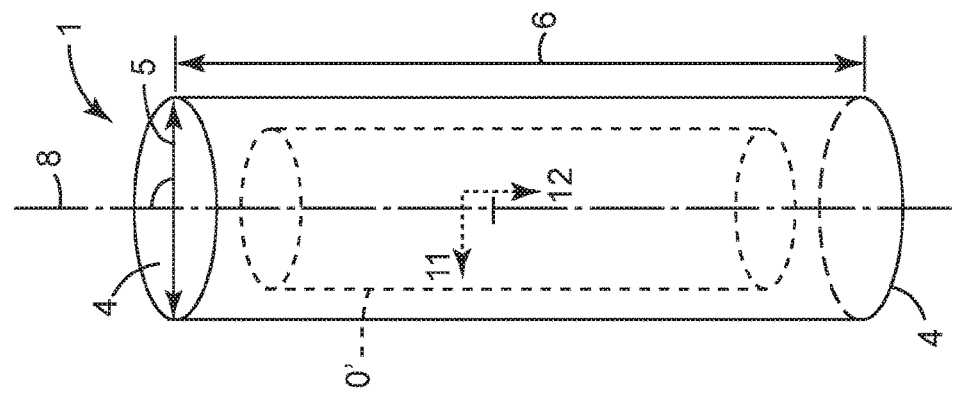
FIG. 1B shows an enlarged section of FIG. 1A.

The process according to the invention is a plasma induced conversion of fluorinated alkanes into fluorinated alkenes. The process is carried out in a plasma reactor. The plasma reactor according to the invention and the process according to the invention will be illustrated by referring to FIG. 1, wherein like elements are provided with the same reference numbers.

The reactor (1') is part of a production line for producing a product stream (14) comprising fluorinated alkenes. The process provided herein produces fluorinated alkenes by the decomposition of fluorinated alkanes in a plasma. Preferably the fluorinated alkenes produced include tetrafluoroethylene (TFE), hexafluoropropylene (HFP) or both.

The reactor (1') comprises in its interior a reactor chamber (1). The reactor chamber (1) is confined by a reactor wall (2). The reactor chamber (1) has a length (6) and a substantially circular cross section (4) having a diameter (5). The length (6) is at least equal to the diameter or greater. The interior part (7) of the reactor chamber (6) contains a longitudinal axis (8) that runs parallel to the length (6) and perpendicular to the cross section (4). The reactor chamber (1) contains, when in use, a reaction zone (0') where the conversion reaction takes place. The reaction zone (0') is created by a plasma (0). The plasma (0) is created by microwaves from a microwave source (13). The microwave energy may be directed to the reactor chamber by a wave guide (15). The plasma (0) in the reaction zone (0') extends along its axial direction (12) and radial direction (11) along the axis (8) in the interior part of the reactor chamber (7). The reaction zone (0') is confined in its radial direction (11) in the area (0') such that is does not contact the reactor walls (2). It is confined in its axial direction to area along the axis (8). The flow conditions in the reactor chamber confining the plasma to area (0') are created by a protection gas flow (9) alone or in combination with the flow of the conversion feed (10). The protective gas feed (9) is introduced into the chamber (1) by the inlet (9a), (9b) or (9c) or a plurality thereof. Inlets (9a,9b,9c) are placed upstream of zone (0'). The inlets are positioned such that the protective gas feed (9) enters the reaction chamber at an angle to the axis (8) and/or to an angle to conversion feed (10). The conversion feed (10) carrying the educts, i.e. the alkanes to be converted is introduced into the chamber (1) by inlet (10a) or a plurality thereof. The conversion feed (10) may alternatively, but preferably additionally, introduced into the chamber (1) via a remote inlet (10b) located at a down-stream position at the end of zone (0') or after zone (0'). A conversion to alkenes takes places in the reaction zone (0') where a product stream (14) is generated. Preferably, the conversion is carried out in the absence of solid particles in the conversion feed (10) and/or in the reaction zone (0') and in particular, the reactor and its reaction chamber is not a fluidized bed reactor containing a fluidized bed containing solid particles. The product stream (14) exits the reactor chamber (1) via the outlet (14a). It may then enter a quenching unit (16) for subjecting it to quenching and may subsequently been directed to a purification step.

The dimensions of the reactor and its chamber depend on the intended throughput and production rate for the desired product, as well as on the applied frequency of the microwave radiation.

The reactor and the process and their components will now be described in greater detail.

The Plasma (0)

A plasma is formed when a gas is ionized. The presence of charge carriers makes the plasma electrically conductive so that it responds strongly to electromagnetic fields. Since the generated plasma generally emits a glow it is also visually observable.

Preferably the plasma (0) is a microwave plasma, which means it is generated by microwave radiation. It is advantageously generated from a gas. Generally, any ionizable gas can be used to generate the plasma (0). Preferably a gas is used that is chemically inert to the conversion reaction of the process. Preferably, the gas can be ionized easily. A preferred gas has a $1^{st}$ ionization energy is in the range of from 1 to 20 eV, e.g. from 1 to 10 eV, or from 10 to 20 eV. Examples of suitable gases include noble gases. A preferred gas is argon.

Formation and maintenance of a microwave plasma is known in the art. Typically, a microwave plasma (0) is generated by supplying energy to the gas from a microwave source (13). Any microwave source can be used that provides microwave radiation sufficient to ignite and perpetuate the microwave plasma. Typical microwave sources useful for plasma application include, e.g. drift tubes, klystrons or magnetrons. Magnetrons are the preferred source.

Microwaves generally have wavelengths in the range of from 1 mm to 1 m, which corresponds to a frequency range of from 300 GHz to 300 MHz. In principle all microwave radiation within the above range can be used. However, for practical reasons, frequencies selected from the industrial, scientific and medical (ISM) radio bands, which are reserved internationally for the use of radio frequency (RF) energy for industrial, scientific and medical purposes other than telecommunications are used. Preferably frequencies of 915 MHz, 2.45 GHz or 5.8 GHz are used, more preferably, 915 MHz and 2.45 GHz.

The microwave radiation may be pulsed or continuous (continuous wave, cw). Preferably, the microwave radiation is continuous.

The microwave source (13) may be arranged outside the reactor chamber (1). The microwave radiation may be directed and supplied to the reactor chamber (1) by a waveguide (16). Wave guides are typically hollow structures of cylindrical or conical shape or coaxial lines and are known in the art. The waveguide (16) and reactor chamber (2) may be arranged such that the longitudinal axis of the waveguide (16) is perpendicular to the longitudinal axis (7) of the reactor chamber (2). The longitudinal axis of the reactor chamber (2) may also be parallel to the longitudinal axis of the waveguide (16) or in another way. A typical waveguide may have a round shape, and an inner diameter in the range of up to about 120 mm, e.g., about 80 mm to about 100 mm.

The reactor chamber (1) is inserted into a metal chamber (2'), which may function as a resonator.

The microwave plasma may be ignited by any means known in the art including supplying microwave radiation in the presence of particles or fibers, combining microwave irradiation with laser, piezo sparks, or by combining microwave irradiation with pressure reduction. Preferably, the microwave plasma is ignited by subjecting the ionizable gas to a pressure reduction in combination with microwave irradiation. For. Example, the pressure in the reactor chamber may be reduced to a range of from about 0.1 mbar to about 500 mbar, preferably from about 1 mbar to about 100 mbar, more preferably from about 5 mbar to about 50 mbar, more preferably from about 10 mbar to 20 mbar. After ignition of the plasma, the pressure in the reactor may be increased to a pressure which allows the intended reaction to be performed while still maintaining the plasma. Typically, such a pressure range may be from about 0.01 bar to about 10 bar, more preferably of from about 0.8 bar to about 1.2 bar.

Reactor Chamber (1)

The plasma (0) is generated in the reactor chamber (1) of the reactor (1'). The reactor chamber is at least partially confined by a reactor wall (2). The reactor wall (2) may not be identical with the wall of the reactor (1') and in fact the reactor wall (2) may be surrounded, at least partially, by a wall (2') of the reactor (1'). Such a wall (2') may be a metal chamber or may be part of a metal chamber. Such metal chamber may function as a resonator for the microwave energy. The reactor wall (2) contains inlets and outlets and may contain an inspection window to visually observe the plasma (0). The reactor chamber (1) is designed to hold a reaction involving a plasma initiated and sustained or only sustained by microwave energy. The reactor chamber (1) and its reactor wall (2) satisfy these conditions and are designed to withstand the operating conditions also. The reactor wall (2) thus preferably is durable under temperature and reagent conditions present in the reaction chamber. Microwave radiation must be able to reach the reaction zone in the reactor chamber such that the plasma (0) can be generated and maintained. In cases where the microwave radiation reaches the reaction zone (0') through the reactor wall (2) (and not exclusively through a wave guide (16) placed in the reaction chamber (1) or connected to the central part of the reaction chamber (1), the reactor wall (2) may allows a sufficient amount of the radiation to penetrate it to reach the reaction zone (0'). Preferably, the reactor wall (2) comprises (or consists of) an area that is microwave-transparent. In one embodiment the entire reactor wall (2) is transparent to microwaves. A microwave-transparent area or material typically has a real part of complex permittivity $\varepsilon_r'$ (at 25° C. and 1-10 GHz) of greater than 0 and up to 10 and an imaginary part of complex permittivity $\varepsilon_r''$ (at 25° C. and 1-10 GHz) of greater than 0 and up to 0.001. For many materials the complex permittivity is available in standard reference textbooks. Examples of microwave-transparent materials include alumina, quartz glass, polytetrafluoroethylene, polyethylene, polypropylene, and boron nitride.

It may not be necessary for the entire reactor wall (2) to be transparent to microwaves. Therefore, the reactor wall (2) can comprise at least one area which is transparent to microwaves, while being less transparent, substantially not transparent or not transparent to microwaves in at least one other area. Preferably the area which is transparent to microwaves is coherent. Preferably, the reactor wall (2) exhibits an area which is transparent to microwaves which covers at least 5% of the total area of the reactor wall (2), preferably at least 20% of the total area of the reactor wall (2), more preferably at least 40% of the total area of the reactor wall (2), more preferably at least 60% of the total area of the reactor wall (2), more preferably at least 80% of the total area of the reactor wall (2), more preferably at least 90% of the total area of the reactor wall (2).

The reactor chamber (1) may have a circular or a substantially circular cross section (4), (e.g., an elliptical, a semicircular cross section or a cross section that can be best approximated by a circular, semicircular or elliptical shape). A circular or substantially circular cross section reduces the formation of deposits on the reactor wall compared to other cross-sections. A substantially circular cross section of the reactor chamber (1) facilitates to control the gas flow in the reactor chamber (1). The reactor chamber (1) further has a length (6) perpendicular to its cross section (14). The length (6) is equal, preferably greater than the diameter (5) of the cross section (4). Compared to circular cross sections, substantially circular cross sections may have several diameters in which case the longest diameter is referred to herein as diameter (5). In a preferred embodiment the reactor chamber (1) is tubular, more preferably linearly tubular, meaning it is not bend or S-shaped.

The reactor chamber (1) may have a cross section (4) with a constant diameter (5) over the whole length (6) of the reactor chamber (1) or a diameter (5) that varies along its length (6), the latter being less preferred. For applications of a microwave frequency in the order of 2.45 GHz the reactor chamber, preferably has an inner diameter from about 3 mm to about 86 mm, preferably from 15 mm to 42 mm.

The length (6) of the reactor chamber (1) should be long enough to contain the entire reaction zone (0') of the process according to the invention. The length of the reaction zone may be dependent on the flow velocity of the conversion feed and the protective gas feed, and the power of the microwave radiation supplied to the reactor chamber (1). In principle, the conversion of the educts may be increased by using a higher flow velocity of the conversion feed (10) and supplying greater microwave power. This may increase the length of the reaction zone and requiring a greater length (6) of the reactor chamber (1) to fully contain the reaction zone (0'). Desirably, the product stream (14) generated in the reaction zone (0') exits the reaction chamber (1) as soon as possible to be subjected to quenching. This may reduce or avoid undesired side reaction taking place and may improve the yield of the desired fluorinated alkenes. Therefore, the upper limit for the length (6) of the reactor chamber (1) may be chosen such that the retention time of the product stream (14) in the reactor chamber (1) is minimized. For example the length (6) of the reactor chamber (6) may be the same or only somewhat greater than that of the reaction zone created in the reaction chamber. In some cases it may be necessary to limit the length (6) of the reactor chamber (1) such that the reactor chamber essentially ends where the reaction zone ends to allow immediate processing of reaction products. However, in other cases it may be advantageous to extend the length (6) of the reactor chamber (1) beyond the length of the reaction zone.

In a typical embodiment for a reaction taking place by a plasma (0) generated with a microwave frequency of 2.45 MHz, the reactor chamber (1) has a length (6) from about 22 mm to about 250 mm, more preferably from about 43 mm to about 160 mm.

In another embodiment of the present invention, microwave radiation with a frequency of 915 MHz is applied. Generally, all of the above considerations valid for microwave radiation with a frequency of 2.45 GHz also apply for the case of microwave radiation of 915 MHz. The reactor chamber in this embodiment preferably has an inner diameter in the range of from about 20 mm to about 600 mm, e.g., from about 100 mm to about 450 mm, or from about 200 mm to about 300 mm. The length of the reactor chamber is at least about 120 mm, e.g., at least about 500 mm. Upper limits for the length include depending on the desired reaction conditions, from about 300 to about 2000 mm or about 500 to about 1700 mm. The distance between the at least one inlet for a protective gas feed and the beginning of the reaction zone is typically no more than about 100 mm, more preferably, about 0 mm. For the above mentioned conditions the outlet diameter is preferably in the range of from about 10 mm to about 86 mm, more preferably in the range of from about 15 mm to about 50 mm.

Protective Gas Feed (9)

Figure 2A:
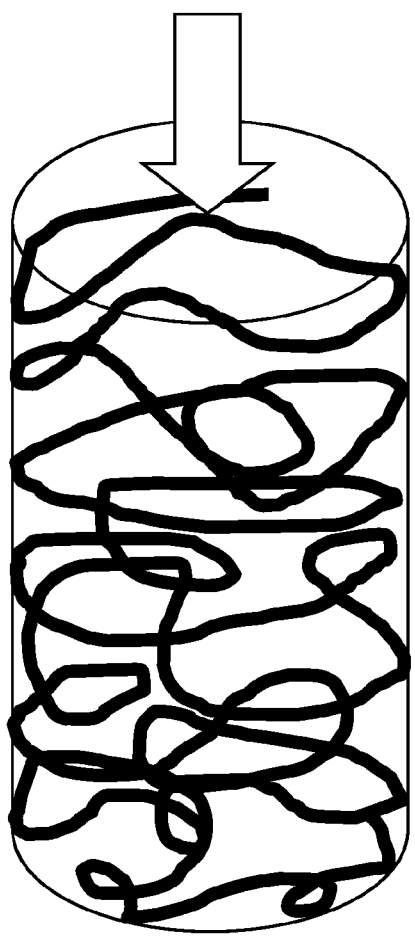
FIG. 2A provides a schematic representation of a reaction zone not according to the present invention.

A protective gas is introduced in the reactor chamber (1) as protective gas feed (9). The protective gas is introduced such that the reaction zone (0') is controlled in volume and length to provide a zone with a high plasma concentration confined to a limited space. Preferably, the reaction zone (0') is confined to the central inner part (7) of the reactor chamber (1). Since the generated plasma (0) generally emits a glow, the reaction of the plasma to the introduction of the protective gas flow can be observed visually. Without the protective feed (9) the plasma (0) in the reaction zone (0') appears to contain several separate moving and intertwining filaments. A schematic representation of a plasma without protective feed (9) as described herein I shown in FIG. 2A. The cylinder in FIG. 2A represents a reaction zone, for example, reaction zone (0'). The arrow in FIG. 2A represents a gas feed to maintain a plasma. The plasma itself is represented by the intertwining line.

Figure 2B:
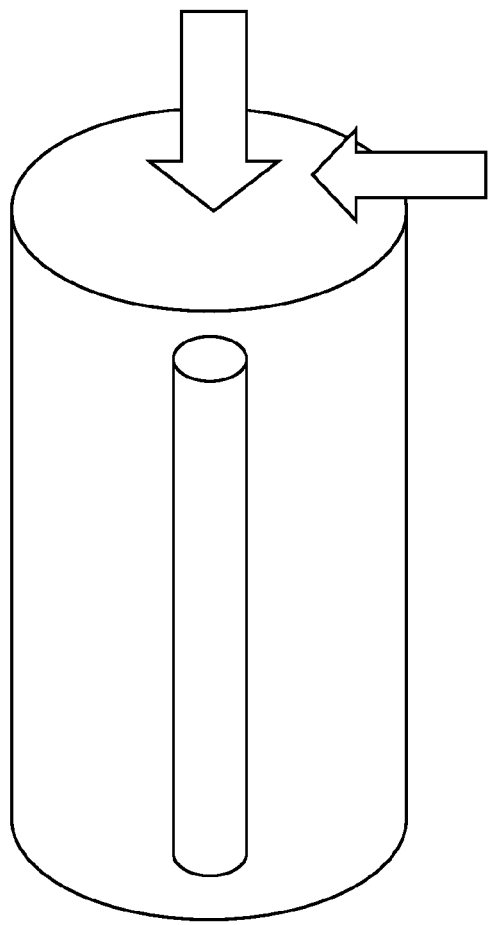
FIG. 2B shows a schematic representation of a confined reaction zone according to the invention.

By introducing a protective gas flow the plasma filaments begin to coalesce, until an essentially stable, central plasma beam is formed which shows a distinct reduction in fluctuation or no fluctuation at all. The plasma becomes essentially stable with regard to its location in the central region along the longitudinal axis of the reactor, forming the reaction zone (0'). The plasma (0) can thus be confined in its axial direction (12) to an area along the longitudinal axis (7) and in its radial direction (11) to the inner, preferably central area of the reactor chamber (1) staying away from the reactor wall (2). The axial direction (12) of the plasma (0) extends along the longitudinal axis (8) of the reactor chamber and its radial direction is perpendicular to its axial direction. The plasma (0) forming the reaction zone (0') can be confined in its radial (11) and axial (12) direction to the inner part (7), preferably central part of the reactor chamber (1). A schematic representation of a plasma as described above is shown in FIG. 2B. FIG. 2B shows the same set up as FIG. 2A, except that the second arrow represents a protective gas feed, for example a gas feed (9). Instead of an intertwining plasma as shown in FIG. 2A, the plasma is now confined to the central area of the reaction zone. The confined plasma is represented in FIG. 2B as the dark solid cylinder.

It is believed that the coalescence of the plasma is the result of a vortex being formed by the protective gas flow. Coalescence of the plasma is a means to control whether the protective gas flow is introduced into the reactor with conditions allowing for optimal reaction conditions. Preferably, the vortex extends along the longitudinal axis (8) of the reactor chamber (1). Thereby, the plasma filaments of the generated plasma (0) may arrange along the longitudinal axis (8) of the reactor chamber (1). Preferably, the plasma filaments are arranged along the vortex. Thereby, the vortex allows constriction of the filaments to form a thick plasma beam which is stable in location and longitudinal extension. Preferably, the filaments are constricted such that the filaments are concentrated at the point of the highest field strength and the highest microwave concentration The effect of concentrating the plasma filaments by introducing the protective gas feed (9) may be increased by superimposing a magnetic field. The superimposed magnetic field may be applied advantageously by a combination of microwave frequency radiation and radio frequency radiation. The radio frequency radiation may be applied by any means known in the art, e.g. by a radio frequency coil.

The protective gas feed (9) is provided such that it flows in the reactor chamber (1) to create and/or maintain the confined reaction zone (0') described above. The protective gas should be supplied to the reactor chamber such that the desired continuous reaction zone (0') is created. The protective gas feed is supplied to the reaction chamber (1) through one or more than one inlet (9a), (9b), (9c). In case of two or more inlets (9a), (9b), (9c), at least two of them may be located in one plane perpendicular to the longitudinal axis (8) of the reactor chamber (1). Preferably, all inlets for the protective gas feed are located in one plane perpendicular to the longitudinal axis of the reactor chamber (1). The inlets may be arranged in a pattern that is rotation-symmetric. For example, in case of two inlets (a first and a second inlet) arranged in the same plane a hypothetical rotation by 180 of the position of the first inlet by 180° within this plane results in the first inlet being at the position of the second inlet. In case of three inlets (first, second and third inlet), a hypothetical rotation by 120° C. of the first inlet in the same way would bring the first inlet to the position of the second inlet and a hypothetical rotation of the first inlet by 240° would bring the first inlet to the position of the third inlet.

Preferably, the at least one inlet (9a), (9b) or (9c) for the protective gas feed (9) is configured such that the protective gas feed (9) enters the reactor chamber (1) at an angle of 45° to 135° with the longitudinal axis (8) of the reactor chamber (1). This angle may result from interaction of flow of the protective gas feed (9) with the flow of a conversion feed (10). Preferably, the one or more inlets (9a) are configured such that the protective gas feed (9) enters the reactor chamber (1) at an angle with the longitudinal axis (8) of the reactor chamber of 110° to 65°, more preferably 90° to 75°, under the flow conditions present in the reactor chamber (1) when the reactor (1') is in continuous use. Preferably, the protective gas feed (9) is introduced into the reactor chamber (1) at an angle of 90° relative to the longitudinal axis (8) of the reactor chamber (1), i.e., perpendicular to the longitudinal axis (8).

Preferably, the one or more inlets (9a), (9b), (9c) for the protective gas feed (9) are positioned upstream of the reaction zone (0'). Preferably, the distance between the at least one inlet (9a), (9b) or (9c) and the reaction zone (0') is short to maintain the momentum of the protective gas feed (9). Preferably, the distance between the at least one inlet (9a) (9b) or (9c) and the beginning of the reaction zone (0) should not exceed 10 cm. More preferably the distance between the at least one inlet (9a) and the beginning of the reaction zone (0) is less than about 50 mm, preferably even smaller, e.g, about 10 mm or less, in some cases even about 0 mm.

Preferably, the one or more inlets (9a), (9b) or (9c) for the protective gas feed are positioned such that they introduce the protective gas stream (9) in a position before the conversion feed (10) enters the reaction chamber (2), i.e. upstream with respect to the conversion feed, at the same height.

The inner diameter of the at least one inlet (9a), (9b), (9c) is typically in the range of from about 1 mm to about 12 mm, more preferably in the range of from about 2 mm to about 6 mm.

The protective gas feed (9) may have a density from 0.1 kg/m$^3$ to 10.0 kg/m$^3$, e.g. from 0.5 kg/m$^3$ to 8.5 kg/m$^3$, or from 1.0 kg/m$^3$ to 6.0 kg/m$^3$, or from 1.5 kg/m$^3$ to 4.5 kg/m$^3$. The "density" in the context of the present invention is to be understood as the standard density, i.e. at 0° C. and 1.01325 bar. Further, it is preferred that the protective gas feed (9) has a boiling point which differs sufficiently from the boiling point of the product gas(es) to facilitate a subsequent purification of the product gas(es) by rectification. Preferably, the protective gas feed (9) comprises at least one compound selected from the group consisting of inert gases, fluorinated alkanes, hydrogen, steam and a combination of two or more thereof. Inert gases include helium, neon, argon, nitrogen, and mixtures thereof are used. Preferably, the inert gas is argon. As fluorinated alkanes, any fluorinated alkane may be used which is in a gaseous or liquid aggregate state under the operation conditions of the present process. Preferably, the fluorinated alkane is tetrafluoromethane, difluorocholormethane, or a mixture thereof. More preferably the fluorinated alkane is tetrafluoromethane. Suitable fluorine scavengers are hydrogen and difluoromethane.

According to one aspect of the present invention, wherein the applied frequency is 2.45 GHz, the flow rate of the protective gas feed (9) within the process is in the range of from 1 L/min to 50 L/min, preferably in the range of from 5 L/min to 25 L/min, more preferably in the range of from 10 L/min to 15 L/min.

Processes lacking a protective gas feed (9) as described above may lead to compounds generated within the process adhering to the interior surface of the reactor wall (2). This so-called "reactor fouling"—can cause problems, such as side reactions started on the undefined surface and, hot-spots created on the reactor wall (2) decreasing the service life of the reactor wall, or even total failure of the reactor wall due to overheating. Such overheating may result from deposition of side products such as carbon on the interior surface of the reactor wall (2) in combination with a coupling of the microwaves into said side products on the surface of the reactor wall (2). Possible deposits of solid material on the surface of the reactor wall also decrease its microwave-transparency.

These problems are at least substantially prevented or reduced by the protective gas feed (9) according to the present invention. Therefore, the microwave-transparency of the reactor wall 1 preferably decreases by less than 5%, more preferably by less than 2%, more preferably by less than 1%, more preferably by less than 0.1% per hour, per day, per week or per month of operation—depending on the reactor design. Preferably, the microwave-transparency of the reactor wall (2) shows substantially no decrease during the operation of the present process.

Conversion Feed (10)

The conversion feed (10) introduces the reactants to the reaction zone (0') for their conversion to fluorinated alkenes. The conversion feed (10) is contacted with the plasma (0) in the reaction zone (0') to generate product stream (14). It may pass through or along the plasma (0) in the zone (0'). Preferably the conversion feed (10) is passed through the plasma (0). In one embodiment an additional conversion feed (10) may be brought in contact with the fading tail of the plasma, i.e. towards the end of the plasma. This may improve the yield of the desired products by suppressing undesired side reactions in the fading tail zone of the plasma.

The conversion feed (10) comprises at least one fluorinated linear or branched alkane having from 1 to 10 carbon atoms. The at least one fluorinated linear or branched alkane has preferably from 1 to 8 carbon atoms, more preferably 1 to 6 carbon atoms, and more preferably 1 to 4 carbon atoms. Preferably, the at least one fluorinated linear or branched alkane has 1, 2, 3 or 4 carbon atoms. Examples for the at least one fluorinated alkane are provided based on the structures of the corresponding hydrocarbons, e.g., methane, ethane, propane, n-butane, isobutane, n-pentane, isopentane, neopentane, n-hexane, 2-methyl pentane, 3-methyl pentane, 2,2-dimethyl butane, 2,3-dimethylbutane, n-heptane, 2-methylhexan, 3-methyl hexane, 2,2-dimethyl pentane, 2,3-dimethyl pentane, 2,4-dimethyl pentane, 3,3-dimethyl pentane, 3-ethyl pentane, and 2,2,3-trimethyl butane.

Preferably, the conversion feed (10) comprises at least one fluorinated linear alkane of formula (I)

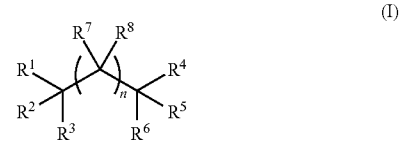

(I)

wherein $R^1$ to $R^8$ are independently of each other H or F, and wherein n is an integer in the range of from 0 to 8. Preferably, n is an integer in the range of from 0 to 7, more preferably of from 0 to 6, more preferably of from 0 to 5, more preferably of from 0 to 4, more preferably of from 0 to 3, more preferably of from 0 to 2. Preferably, n is 0, 1, or 2.

Preferably, the at least one fluorinated linear or branched alkane present in the conversion feed (10) is in a gaseous or liquid state. Preferably, it is in a gaseous state. It is most preferred that all fluorinated linear or branched alkanes present in the conversion feed are in a gaseous state.

Generally, the concentration of the at least one fluorinated linear or branched alkane in the conversion feed is sufficient to allow the conversion to be performed. Preferably, the concentration of the at least one fluorinated linear or branched alkane in the conversion feed (10) is from about 5 to about 100 volume percent (hereinafter vol %), e.g. in the range of from about 30 to about 95 vol %, or from about 50 to about 90 vol %, or from about 80 to about 85 vol %.

The conversion feed (10) may also comprise at least one further gas. Preferably, gases are comprised which exhibit a beneficial influence on the process, such as an increase of the yield regarding the desired fluorinated alkene, an increase of the turnover, an increase of the stability of the plasma, a better temperature control, a better control of the plasma volume, and so on. Preferably, the further gas is selected from the group consisting of hydrogen, carbon monoxide, carbon dioxide, difluoromethane, and argon or a combination of two or more thereof. In some preferred cases the further gas is hydrogen or carbon monoxide, where carbon monoxide can be even more preferred. It may be advantageous if the conversion feed (10) further comprises a compound which is suitable to serve as a gas for generating the microwave plasma. Thus, it can contribute to the smooth progression of the reaction if also argon is present in the conversion feed. The concentration of the further gas or the mixture of further gases in the conversion feed is typically in the range of from about 0 to about 95 vol %, e.g. in the range of from about 5 to about 70 vol %, or from about 10 to about 50 vol %, or from about 15 to about 20 vol %.

The flow rate of the conversion feed (10) is typically chosen to provide a residence time in the reaction zone (0') sufficient for the conversion reaction to provide good yields. Preferably, the residence time of the conversion feed (10) is from 0.1 to 3000 ms, preferably from 1 to 150 ms, more preferably from 5 to 15 ms. The flow rate of the feed (10) may additionally be adapted to the flow rate and flow behavior of the protective gas feed (9) to create or maintain the confined reaction zone (0') described above. In the process according the present invention, it can further be preferred to use a ratio of the flow rate of the protective gas feed (9) to the flow rate of the conversion feed (10) of about 1 to about 1,000, preferably from about 50 to about 700, e.g. from about 100 to about 400, or from about 400 to about 700.

Preferably the conversion feed (10) is passed through the reactor continuously.

In one embodiment of the present invention where frequency of the microwave radiation of 2.45 GHz is applied, the conversion feed (10) has a flow rate in the range of from 5 mL/min to 5000 mL/min, preferably of from 30 mL/min to 500 mL/min.

Generally, the specific energy absorbed by the at least one fluorinated linear or branched alkane comprised by the conversion feed (10) is not restricted. Preferably, the specific energy absorbed by the at least one fluorinated linear or branched alkane comprised by the conversion feed is in the range of from about 1,000 kJ/mol to about 500,000 kJ/mol, more preferably from about 5,000 kJ/mol to about 50,000 kJ/mol, based on the at least one fluorinated linear or branched alkane comprised in the conversion feed. The absorbed specific energy relates to the microwave power absorbed by the at least one fluorinated linear or branched alkane comprised by the conversion feed. The absorbed microwave power is determined based on the applied microwave power and the reflected microwave power. The reflected microwave power can be measured electronically, e.g. by means of a diode, or calorimetrically, e.g. by a calorimetric measurement, such as the water load of an isolator or measurement of the cooling water of the reactor.

The conversion feed (10) is supplied to the reactor chamber (1) via one or more inlets (10a, 10b). The feed (10) flows from the inlet through the reaction chamber (1) via the reaction zone (0) to the outlet (14a) of the reaction chamber (1). The flow velocity of the conversion feed (10) should be such that the desired conversion is achieved while the reaction zone (0') is held stable. The inner diameter of the inlet (10a, 10b) for a conversion feed (10) is typically in the range of from about 0.2 mm to about 16 mm. Preferably, the inner diameter of the inlet for a conversion feed is in the range of from about 1 mm to about 10 mm, more preferably from about 2 mm to about 4 mm for the above mentioned conditions. The inlet (10a) or a plurality thereof are provided such that the conversion feed (10) flows along the longitudinal axis (8) of the reactor chamber (1) or at an angle with it of no more than about 80°, preferably 45° or less, e.g., about less than 10° or less than 5°.

The inlet (10a) preferably feeds the conversion feed (10) to the reactor chamber (1) via an inlet nozzle. Preferably, the ratio of the inner diameter of the reactor chamber and the inner diameter of the inlet nozzle is from about 3 to 1 to about 6 to 1, more preferably about 4:1 to about 5:1. The inlet (10a) can be located upstream of the reaction zone (0') for example directly at the beginning of a reaction zone or at a distance thereto. In case the conversion feed (10) is provided to the reactor chamber by two or more inlets, it is possible to use the different inlets for different conversion feeds (10, 10') having different components or the same components but in different concentrations. It may also be useful to position the inlets (10a) at a distance to the beginning of the reaction zone (0') to allow the different conversion feeds (10,10') to mix. It is also possible to provide the same or different conversion feeds (10) via inlets (10a) at different positions. For example, one inlet (10a) may be located before or at the beginning of the reaction zone (0') and at least one further inlet (10a) may be located after the beginning of the reaction zone, e.g., in the middle of the reaction zone or at the end of the reaction zone or even after the reaction zone has ended. An inlet (10c) located towards or at the end of the reaction zone is referred herein as a "remote inlet". A remote inlet allows feeding in at the fading tail of the plasma and is, therefore, preferably located in sufficiently close proximity downstream with regard to the plasma. The inner diameter of this inlet has typically a dimension to facilitate a gas input in the range of at least one-tenth of the conversion feed to twice of the conversion feed.

Product Stream (14)

The product stream (14) comprises the fluorinated alkenes generated in the reaction zone (0') and is generated after or during the conversion feed (10) is contacted with the plasma (0) in the reaction zone (0'). The product stream (14) exits the reactor chamber (1) via one or more outlets (14a) positioned downstream of the reaction zone (0'). The product stream (14) comprises fluorinated alkenes generated in the reaction zone and may further comprise unreacted reactants and side-products.

The outlet (14a) can be positioned such that the flow direction of the product stream (14) leaving the reactor chamber through the outlet (14a) is essentially parallel to or along the longitudinal axis (8) of the reactor chamber (1). The inner diameter of the outlet (14a) is typically chosen such that undesired back pressure in the reactor chamber (1)

can be avoided or minimized. Generally, the diameter of the outlet (14a) is in the range of the diameter of the reactor chamber (1). For example, the ratio of the diameter of the outlet to the diameter of the reactor chamber may be about 1 to about 0.3, preferably about 0.95 to about 0.7.

The product stream (14), optionally, may be subjected to a quenching step d). Generally, the quenching step may be carried out according to any method known in the art. The quenching step may be carried out continuously or discontinuously or by a combination thereof. However, it may be advantageous if the quenching step is carried out continuous. Depending on the respective quenching method, the product stream (14) is either passed through the cooling medium or the product stream (14) is passed along the cooling medium. The cooling medium may be in a flowing mode as well. In this case the product stream (14) may be either in counterflow or parallel flow mode to the cooling medium.

The cooling medium in step d) may be in a solid (e.g. a cooled wall), a liquid or in a gaseous state. Preferably, the cooling medium is a liquid or a gas. In case of a gas, preferably, at least one inert gas may be used. Further, it is preferred that the gas has a boiling point which differs sufficiently from the boiling point of the product gas(es) so as to facilitate a subsequent purification of the product gas(es) by rectification. Preferably, the cooling medium is a liquid (under conditions of room temperature and atmospheric pressure), such as water or an aqueous solution. More preferably, the cooling medium is an aqueous solution of a fluorine scavenger, such as an aqueous solution of hydrofluoric acid, of potassium hydroxide, of sodium hydroxide or of calcium hydroxide.

The cooling medium may have a temperature of up to about 100° C., preferably of up to about 50° C., before it is contacted with the product stream. Generally, cooling is to be effected such that the time for potential detrimental side reactions or reverse reactions is minimized. As a result, the temperature and amount of cooling medium should be sufficient to effect a very rapid cooling of the product stream. It can thus be preferred if in step d) the product stream (14) is cooled with a cooling rate of from about 10 K/s to about 5000 K/s, preferably about 100 K/s to about 1000 K/s. The temperature of the product stream (14) may be measured by any means known to the skilled person. Examples include resistance thermometers and thermocouples.

Generally, the steps a) to c) of the process according to the invention can be performed in the presence of chlorine, chlorine containing compounds, or chlorine and chlorine containing compounds. However, preferably, the steps a) to c) are performed in the substantial absence of chlorine, chlorine containing compounds, or chlorine and chlorine containing compounds. In a most preferred embodiment the feeds are free of chlorine and chlorine containing compounds. The term "free of chlorine and chlorine containing compounds" as used in this context means that chlorine and chlorine containing compounds are either not contained at all or only contained in traces of impurity. For example, the concentration of chlorine and chlorine containing compounds in the feeds (conversion and protective gas feeds) is in total at most 500 ppm, more preferably at most 100 ppm.

The product stream (14) may be subjected a purification step e). Preferably, the product stream is purified by a thermal separation process, such as distillation, more preferably rectification. Therefore, it is advantageous if the gases used in the present process were condensable within the quenching step, and if these gases had boiling points which are sufficiently different from each other.

The present invention is further illustrated by the following examples without intending to limit the invention to the examples.

EXAMPLES

Figure 1A:
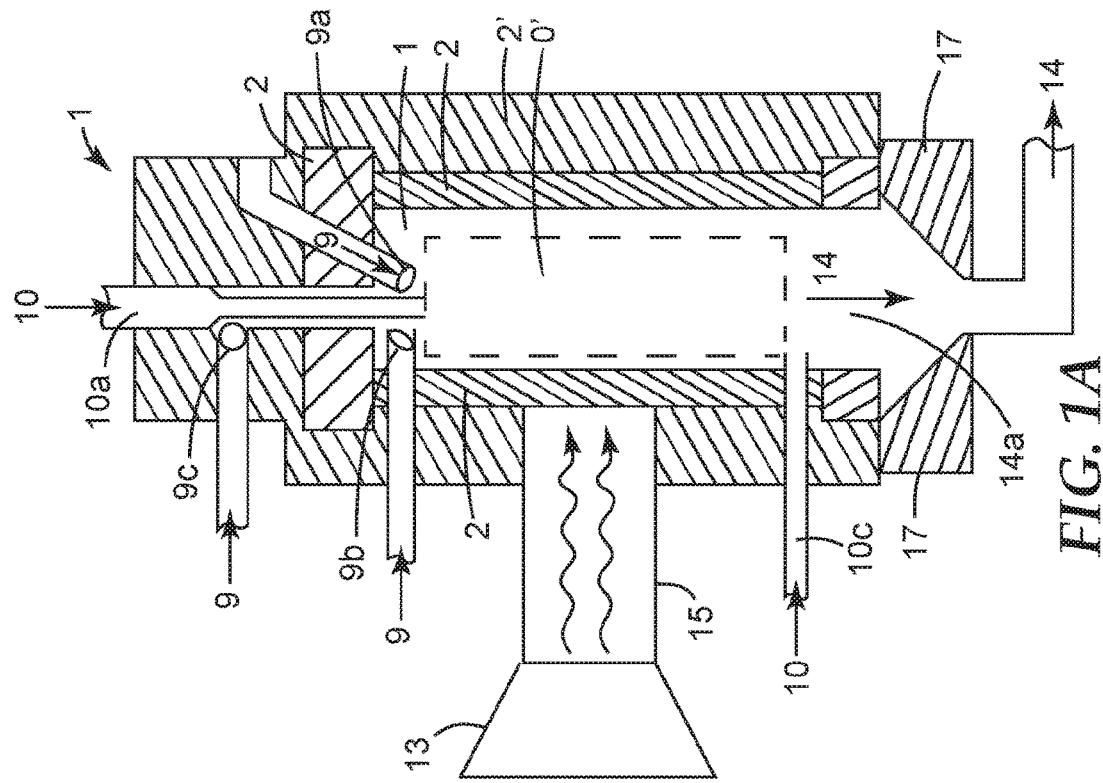
FIG. 1A provides a schematic representation of the process and apparatus according to the present invention.

The examples described hereinafter were carried out in a reactor as shown in FIG. 1A. The reactor contained a tubular quartz glass reactor chamber of a length 94 mm length with an inner diameter of 40 mm. The quartz tube was inserted into a metal chamber as resonator. A microwave source was connected via a wave guide (86 mm width×43 mm height) with the resonator (2). The educts were fed into the reactor chamber along its longitudinal axis by an inlet at the top of the reactor chamber (as shown in FIG. 1a (inlet 10a)). A protective gas feed was introduced into the reactor chamber at an angle of 90° C. to the longitudinal axis of the reactor chamber by an inlet (9c) as shown in FIG. 1A. At the bottom of the reactor chamber the product feed (14) was directed via outlet (14a) into a quenching unit.

Before carrying out the examples the whole apparatus was flushed for 15 minutes with argon. Then, the pressure in the reactor was reduced and set to 15 mbar for 15 minutes. Microwave power of 2200 W (continuous wave (cw)) was applied for 2 minutes (2.45 GHz), whereby a plasma was ignited. Then, the microwave power was decreased to 500 W (cw). Argon was introduced such that ambient pressure was reached.

Example 1

Conversion of n-Perfluorobutane

Figure 3:
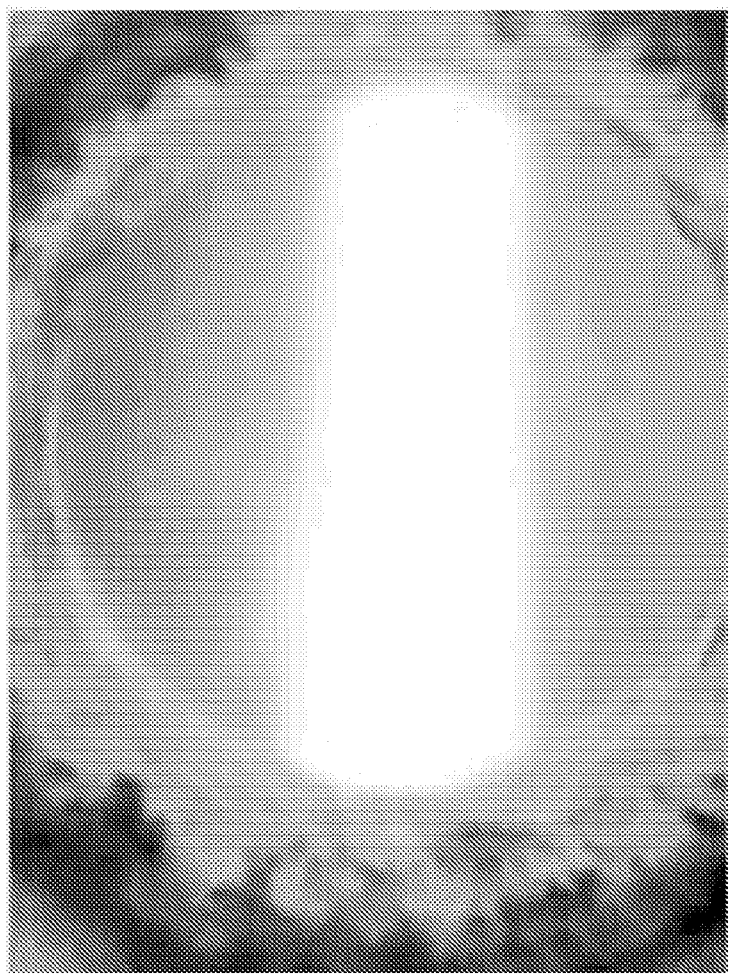
FIG. 3 is an image taken of the reaction zone created in the process described in the experimental section.

By a tangentially introduced Argon flow of 5 L/min a plasma beam was created that was confined to the central area of the reactor chamber. A photograph of the plasma confined to the central area was taken and is shown in FIG. 3. The photograph was taken from a circular observation window in the reactor wall and shows the reactor zone. The bright vertical line in the center of the photograph was the plasma. As shown in the photograph, the plasma was confined to a narrow central area. Via the inlet for the conversion feed, n-perfluorobutane was introduced into the reactor with a flow rate of 35 mL/min. After leaving the reaction zone, the gases were quenched with an aqueous solution of potassium hydroxide. The product gas was analyzed by means of gas chromatography. The composition of the product stream (mole fraction of the reaction products) in dependence of the absorbed microwave power absorbed by the at least one fluorinated linear or branched alkane is given in table 1.

TABLE 1

| P/W | $[C_2F_6]$ | $[C_2F_4]$ | $[C_3F_6]$ | $[C_4F_{10}]$ |
|---|---|---|---|---|
| 110 | 0.53 | 0.11 | 0.04 | 0.32 |
| 120 | 0.57 | 0.15 | 0.06 | 0.23 |
| 170 | 0.60 | 0.18 | 0.08 | 0.14 |
| 200 | 0.61 | 0.20 | 0.08 | 0.11 |
| 250 | 0.61 | 0.22 | 0.08 | 0.09 |
| 300 | 0.59 | 0.21 | 0.07 | 0.13 |
| 320 | 0.59 | 0.24 | 0.07 | 0.10 |

Example 2

Conversion of n-Perfluorobutane in the Presence of 20 Vol % of Hydrogen

By a tangentially introduced argon flow of 5 L/min a plasma beam was created. Via the inlet for the conversion feed, 35 mL/min n-perfluorobutane and 7 mL/min $H_2$ were introduced into the reactor chamber. After leaving the reaction zone, the gases were quenched with an aqueous solution of potassium hydroxide. The product gas was analyzed by gas chromatography. The composition of the product stream (mole fraction of the reaction products) in dependence of the absorbed microwave power absorbed by the at least one fluorinated linear or branched alkane is given in table 2.

TABLE 2

| P/W | $[C_2F_6]$ | $[C_2F_4]$ | $[C_3F_6]$ | $[C_4F_{10}]$ |
|---|---|---|---|---|
| 500 | 0.63 | 0.23 | 0.00 | 0.14 |
| 1,000 | 0.62 | 0.34 | 0.02 | 0.02 |
| 1,500 | 0.62 | 0.35 | 0.03 | 0.00 |
| 2,000 | 0.62 | 0.36 | 0.03 | 0.00 |
| 2,500 | 0.61 | 0.36 | 0.03 | 0.00 |

Example 3

Conversion of n-Perfluoroethane

By a tangentially introduced argon flow of 5 L/min a plasma beam was confined to the central area of the reactor chamber. Via the inlet for the conversion feed, n-perfluoroethane was introduced into the reactor chamber with a flow rate of 35 mL/min. After leaving the reaction zone, the gases were quenched with an aqueous solution of potassium hydroxide. The product gas was analyzed by means of gas chromatography. The composition of the product stream (mole fraction of the reaction products) in dependence of the absorbed microwave power absorbed by the at least one fluorinated linear or branched alkane is given in table 3.

TABLE 3

| P/W | $[C_2F_6]$ | $[C_2F_4]$ | $[C_3F_6]$ |
|---|---|---|---|
| 180 | 0.80 | 0.20 | 0.00 |
| 210 | 0.65 | 0.32 | 0.02 |
| 230 | 0.57 | 0.41 | 0.03 |
| 250 | 0.45 | 0.51 | 0.04 |

Gas Chromatography

Gas chromatography (GC) analysis was carried out on a Hewlett Packard 5890 Series II machine. The column was equipped with "carbopack C Mesh 80/100" and had a length of 6 m. As a carrier, helium was used with a flow rate of 16 mL/min. The reference flow was 60 mL/min. The starting temperature was 40° C. and held for 5 min, then the temperature was raised by 25° C./min up to 110° C. and was kept constant at 110° C. for 10 min. As a detector, a thermal conductivity detector was used.

The retention times were as follows:

| | | | |
|---|---|---|---|
| Ar/$H_2$: | 2.184 min | TFE: | 3.695 min |
| $CF_4$: | 2.403 min | HFP: | 8.000 min |
| $CH_2F_2$: | 3.012 min | OCFB*: | 8.555 min |
| $C_2F_6$: | 3.252 min | | |

*octafluorocyclobutane

The invention claimed is:

1. A process for producing fluorinated alkenes, the process comprising:
    a) providing a microwave plasma, forming a reaction zone in a reactor comprising a reactor chamber at least partially confined by a reactor wall, wherein the reactor chamber has
        a substantially circular cross-section with a diameter and a length, which length is perpendicular to the cross-section and is equal to or greater than the diameter, and
        a longitudinal axis running parallel to the length in a central part of the reactor chamber;
    b) providing a protective gas feed in the reactor chamber, and
    c) contacting a conversion feed comprising at least one fluorinated linear or branched alkane having from 1 to 10 carbon atoms with the plasma to produce a product stream containing a fluorinated alkene;
    wherein the protective gas feed in the reactor chamber flows such that the protective gas feed creates or supports to create a reaction zone that extends in an axial direction along the longitudinal axis of the reactor chamber and wherein the reaction zone is confined in a radial direction, which is perpendicular to the axial direction, to the central part of the reactor chamber such that the reaction zone does not contact the reactor wall.

2. The process according to claim 1, wherein the plasma is generated by a microwave source arranged outside the reactor chamber and the reactor wall comprises a zone which is transparent to microwaves.

3. The process according to claim 1, wherein the protective gas comprises at least one compound selected from the group consisting of helium, neon, argon, nitrogen, fluorinated alkanes, hydrogen, steam, and a combination of two or more thereof.

4. The process according to claim 1, wherein the protective gas feed is introduced into the reactor chamber at an angle with respect to the longitudinal axis, of from 45° to 110°, and further wherein the conversion feed is directed along the longitudinal axis.

5. The process according to claim 1, wherein the plasma is generated by a frequency of 915 MHz or 2.45 GHz or 5.8 GHz.

6. The process according to claim 1, wherein the conversion feed comprises the at least one fluorinated linear or branched alkane in a gaseous state.

7. The process according to claim 1, wherein the conversion feed has a residence time in the plasma in the range of from 1 to 10 ms.

8. The process according to claim 1, wherein the concentration of the at least one fluorinated linear or branched alkane in the conversion feed is in the range of from 50 to 80 vol %.

9. The process according to claim 1, wherein the protective gas feed and the conversion feed are introduced into the reactor chamber at a flow rate ratio of flow rate of the protective gas feed to the flow rate of the conversion feed of from 50 to 700.

10. The process according to claim 1, wherein the pressure in the reactor chamber under continuous operating conditions is kept in the range of from 0.8 to 1.2 bar.

11. The process according to claim 1, additionally comprising:
   d) quenching the product stream comprising the fluorinated alkene.

12. The process according to claim 11, wherein in step d) the product stream is quenched with water or an aqueous solution, wherein the aqueous solution comprises hydrofluoric acid, potassium hydroxide, sodium hydroxide or calcium hydroxide.

13. The process according to claim 11, wherein the product stream is cooled with a cooling rate in the range of from 100 K/s to 1,000 K/s.

* * * * *